United States Patent
Tsai

(10) Patent No.: US 6,615,086 B2
(45) Date of Patent: Sep. 2, 2003

(54) NON-ADHESIVE MASSAGER WITH CONDUCTIVE SILICON

(76) Inventor: Sam Tsai, 4F, No. 14, Lane 281, Sec. 2, Hsi Yuan Road, Taipei (TW)

(*) Notice: Subject to any disclaimer, the term of this patent is extended or adjusted under 35 U.S.C. 154(b) by 34 days.

(21) Appl. No.: 10/010,856

(22) Filed: Dec. 4, 2001

(65) Prior Publication Data

US 2003/0105418 A1 Jun. 5, 2003

(51) Int. Cl.[7] .................................................. A61N 1/00
(52) U.S. Cl. ............................. 607/72; 607/46; 607/48; 601/15; 601/21
(58) Field of Search ............................. 601/15, 20, 21, 601/71, 84; 607/46, 48, 72, 148, 149, 152; 600/393, 394

(56) References Cited

U.S. PATENT DOCUMENTS

| | | | | |
|---|---|---|---|---|
| 4,177,817 A | * | 12/1979 | Bevilacqua | 607/149 |
| 5,397,338 A | * | 3/1995 | Grey et al. | 607/46 |
| 5,643,332 A | * | 7/1997 | Stein | 607/49 |
| 5,922,012 A | * | 7/1999 | Sakano | 607/46 |
| 6,438,428 B1 | * | 8/2002 | Axelgaard et al. | 607/152 |

* cited by examiner

Primary Examiner—Danton D. DeMille
Assistant Examiner—Quang Thanh

(57) ABSTRACT

A massager has a pair of non-adhesive massaging pads and a pair of metal buttons. Each metal button extends between one of the massaging pads and the massaging pulse generator so that the signal from the massaging pulse generator is able to be transmitted to the non-adhesive conductive silicon and thus accomplishes the purpose of massaging.

2 Claims, 6 Drawing Sheets

NON-ADHESIVE MASSAGER WITH CONDUCTIVE SILICON

FIELD OF THE INVENTION

The present invention relates to a non-adhesive massager, and more particularly to a non-adhesive massager with conductive silicon. The massager has metal buttons extending between the massaging pad and a massaging pulse generator so as to transmit the signal from the massaging pulse generator to the massaging pad.

BACKGROUND OF THE INVENTION

With reference to FIG. 1, a conventional massager has multiple adhesive conductive pads 71 and a massaging pulse generator (not shown) in a console 72. Each of the adhesive conductive pads 71 has a wire 711 connecting to the console 72 so that the signal from the massaging pulse generator is able to be controlled and transmitted to each of the adhesive conductive pads 71. This type of massager suffers from the following drawbacks, such as:

1). The massaging area is limited due to the area of each of the adhesive conductive pads. Therefore, if a large area is to be massaged, the quantity of the pads is necessary to be increased.
2). While using this type of massager, the user will have to attach each of the pads on a spot of the body to be massaged. Because each pad needs a wire to receive signal from the console, after the pads are fully attached to the massaging area, there are numerous wires extending around the user, which makes the user difficult to move freely.
3). Because the area of each pad is so small that the massaging effect is doubtful.
4). The adhesion of the pad is easy to cause allergy to the user having allergic skin when using this type of massager.

To overcome the shortcomings, the present invention intends to provide an improved massager to mitigate or obviate the aforementioned problems.

SUMMARY OF THE INVENTION

The primary objective of the invention is to provide a massager having a pair of non-adhesive massaging pads and a pair of metal buttons each extending between one of the massaging pads and the massaging pulse generator so that the signal from the massaging pulse generator is able to be transmitted to the non-adhesive conductive silicon and thus accomplishes the purpose of massaging.

Another objective of the invention is to provide a massager that is able to eliminate the requirement of wires so that the user is able to move freely when massaging with the massager of the present invention.

Other objects, advantages and novel features of the invention will become more apparent from the following detailed description when taken in conjunction with the accompanying drawings.

DETAILED DESCRIPTION OF THE INVENTION

Figure 1:
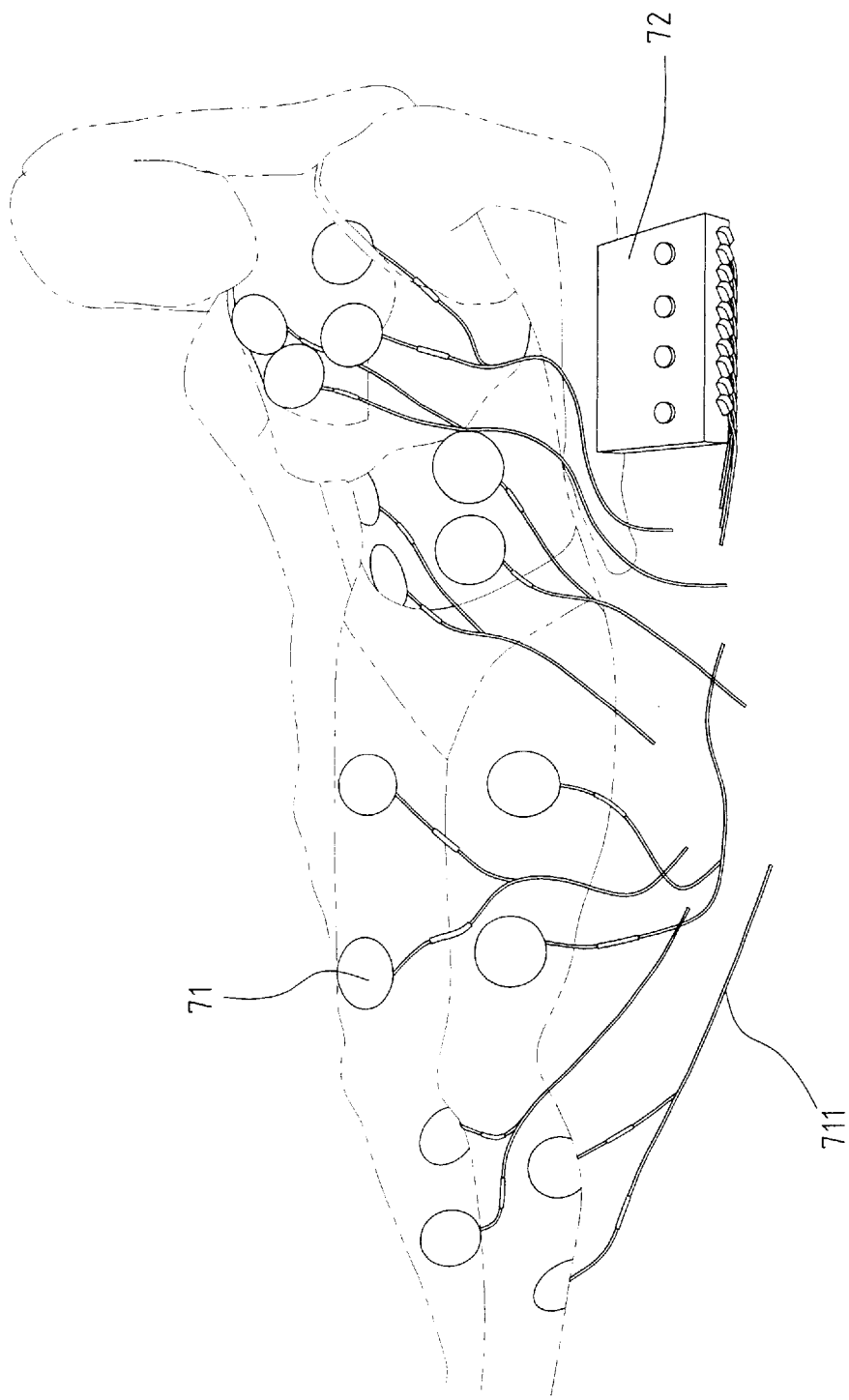
FIG. 1 is a schematic view of a conventional massager applied on the body of the user.
Figure 2:
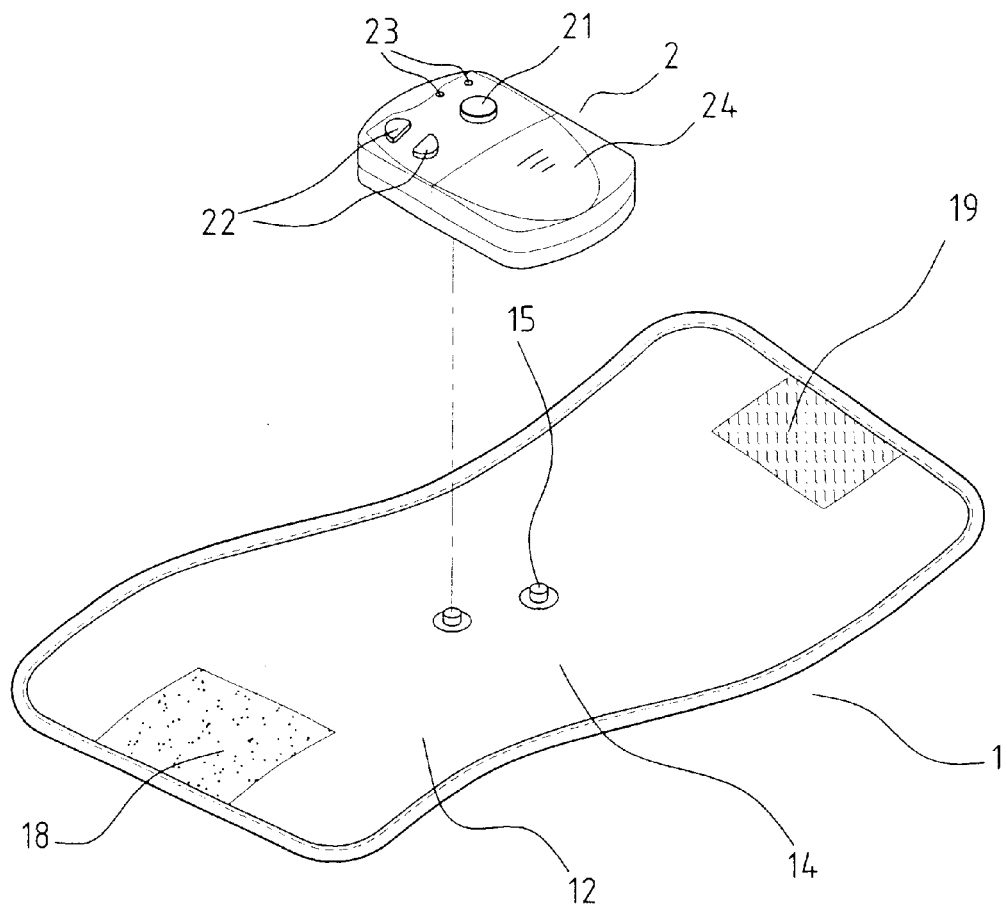
FIG. 2 is an exploded perspective view showing the massaging pad and the massaging pulse generator.
Figure 3:
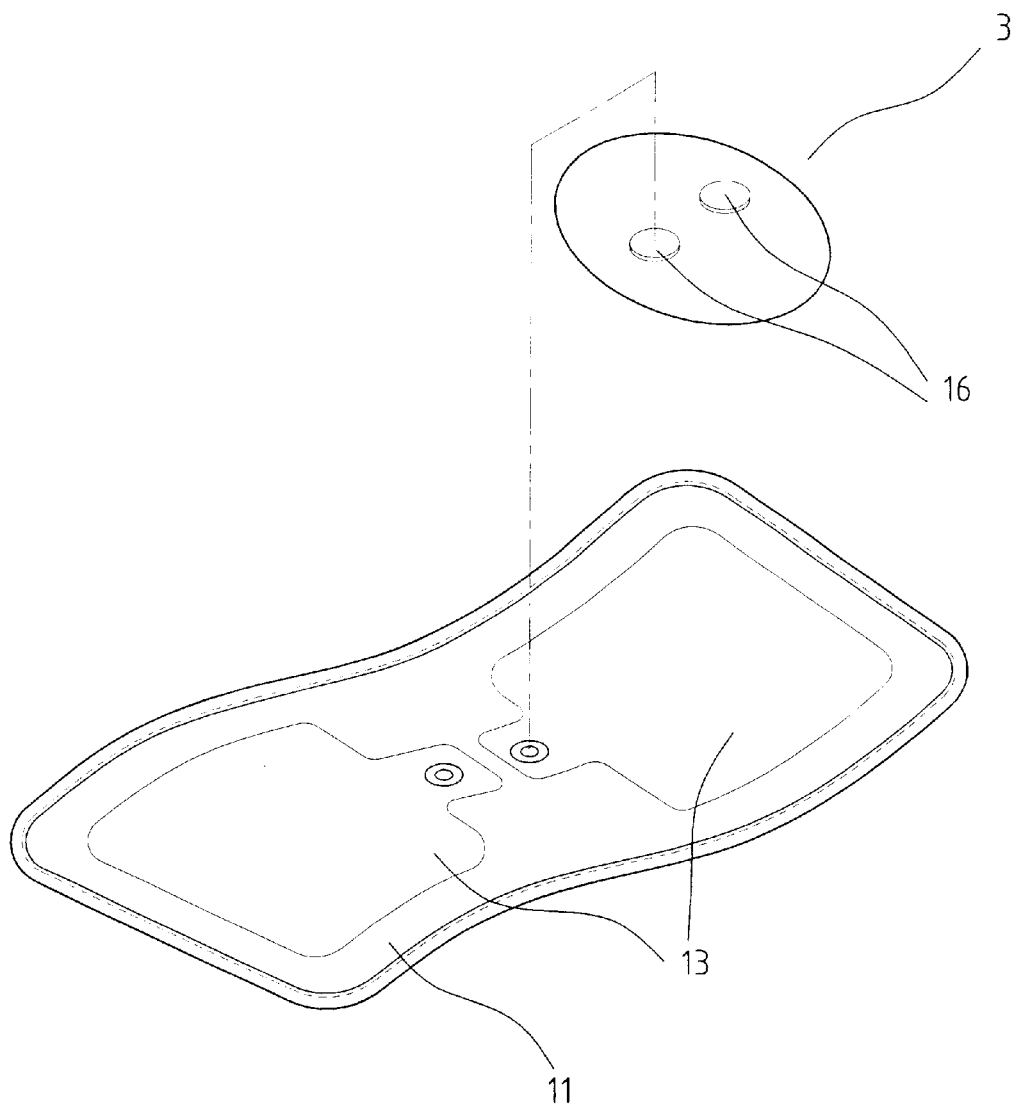
FIG. 3 is an exploded perspective view showing the structure of the reverse side of the massaging pad, wherein a plastic pad is provided to cover the metal buttons.

With reference to FIG. 2 and FIG. 3, the massager in accordance with the present invention has a massaging pad 1 and a massaging pulse generator 2.

The massaging pad 1 has an inner side 11 intended to attach to the user's skin and an outer side 12 to be attached to the massaging pulse generator 2. The inner side 11 has two geometrically corresponding non-adhesive conductive silicon pads 13 securely attached to the inner side 11. The outer side 12 is covered with a non-conductive plastic 14 and is provided with at least one (two are shown in the embodiment) metal button 15 extending through the massaging pad 1. A male and female connector combination 18,19 is respectively provided on two opposite end sides of the outer side 12. The massaging pulse generator 2 has at least one massaging mode switch 21, a signal strength adjusting buttons 22, indicators 23 and a battery compartment 24. On the bottom side of the massaging pulse generator 2 has recesses (not shown) defined to correspond to the at least one metal button 15 so that the massaging pulse generator 2 is able to engage with the at least one metal button 15.

On the inner side 11, a plastic pad 3 is provided to cover the bottom end of the at least one metal button 15. The plastic pad 3 has at least one small non-adhesive conductive pad 16 located to correspond to the at least one metal button 15 so that after the plastic pad 3 is applied to cover the at least one metal button 15, the at least one small non-adhesive conductive pad 16 is able to transmit the signal from the massaging pulse generator 2 to the non-adhesive conductive silicon pads 13.

Figure 4:
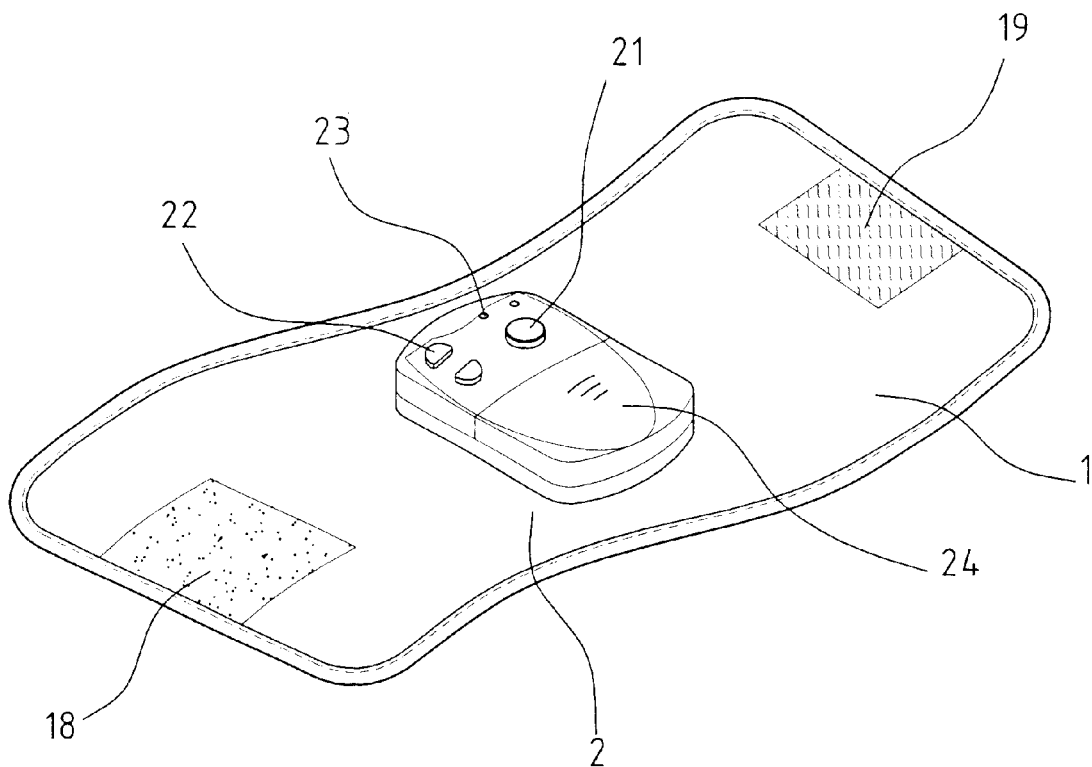
FIG. 4 is a perspective view of the massager of the present invention.

With reference to FIG. 4, after the massaging pulse generator 2 is engaged with the at least one metal button 15, the massager of the present invention is assembled an ready for use.

Figure 5:
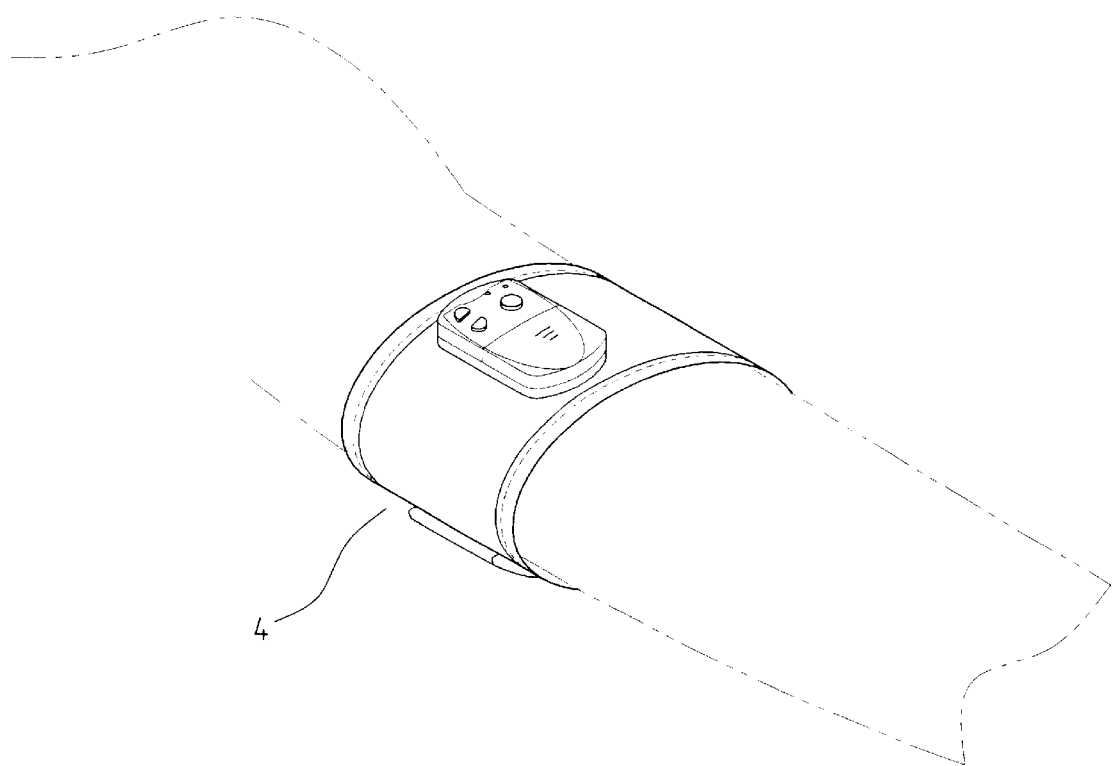
FIG. 5 is a schematic view of the massager in use.
Figure 6:
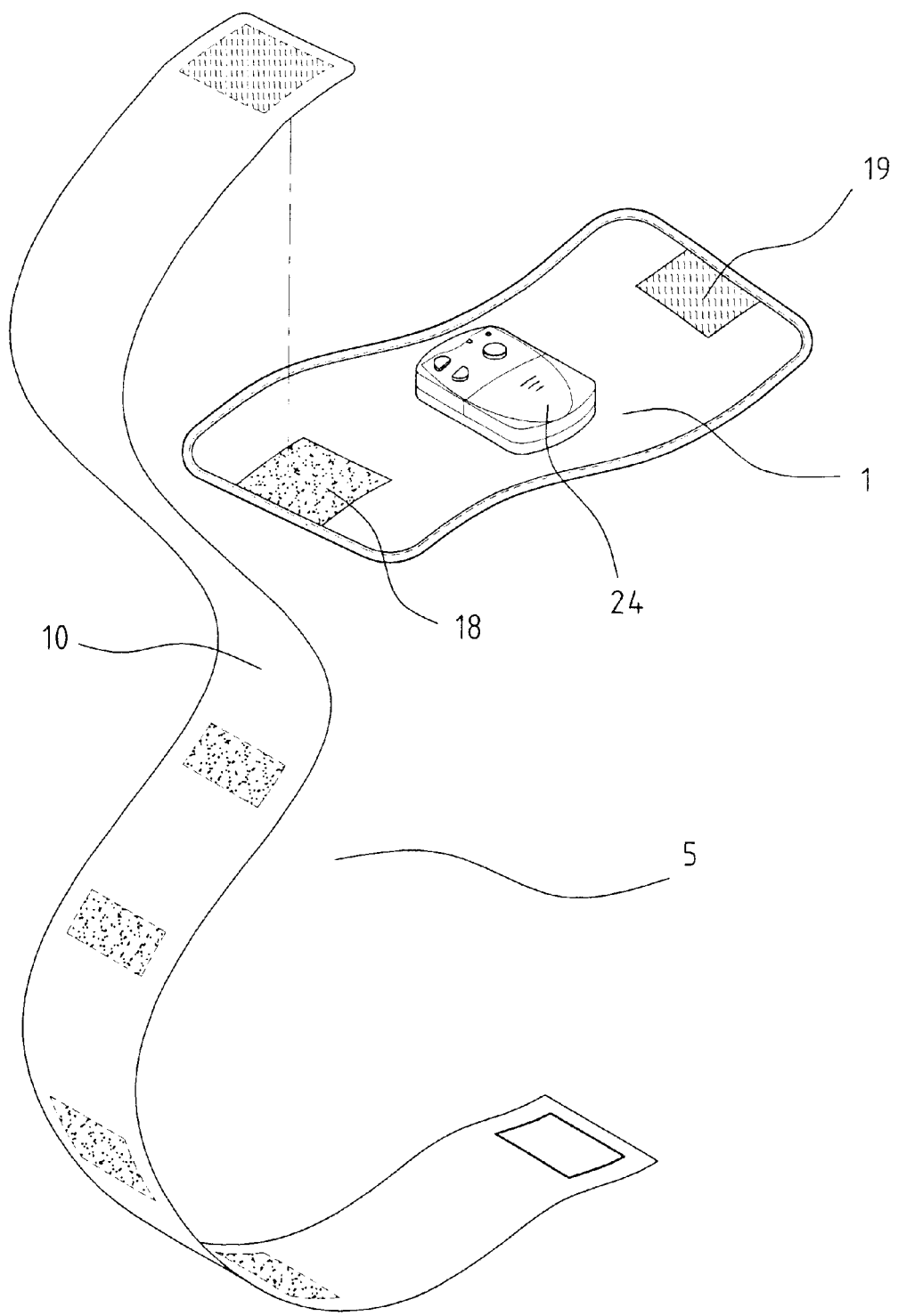
FIG. 6 is an application of the massager, wherein a long adhesive belt is provided to the massager so that the user is able to attach the massager to a large area of the body.

With reference to FIGS. 5 and 6, the user is able to use the male and female connector combination 18,19 (not shown in both FIGS. 5 and 6) to engage opposite end sides of the massaging pad 1. Yet, when the length of the massaging pad 1 is not enough to wrap around a specific area of the user's body, the user is able to use an auxiliary band 10 to engage with opposite end sides of the massaging pad 1 to fulfill the user's need.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A massager composed of non-adhesive conductive silicon pads, the massager comprising:

a massaging pad having an inner side adapted to attach to a user's skin and an outer side adapted to be attached to a massaging pulse generator, wherein the inner side has two geometrically corresponding non-adhesive conductive silicon pads securely attached to the inner side, the outer side is covered with a non-conductive plastic and is provided with at least one metal button extending through the massaging pad, a male and female connector combination is respectively provided on two opposite end sides of the outer side;

wherein the massaging pulse generator has at least one massaging mode switch, a signal strength adjusting buttons, indicators and a battery compartment, wherein on a bottom side of the massaging pulse generator has recesses defined to correspond to the at least one metal button so that the massaging pulse generator is able to engage with the at least one metal button;

wherein on the inner side a plastic pad is provided to cover a bottom end of the at least one metal button, wherein the plastic pad has at least one small non-adhesive conductive pad located to correspond to the at least one metal button so that after the plastic pad is applied to cover the at least one metal button, the at least one small non-adhesive conductive pad is able to transmit the signal from the massaging pulse generator to the non-adhesive conductive silicon pads.

2. The non-adhesive massager as claimed in claim 1, further comprising an auxiliary band detachably connected to the male and female connector combination so as to be wrapped around a specific area of the user's body.

\* \* \* \* \*